United States Patent [19]

Hamburg

[11] Patent Number: 4,883,454
[45] Date of Patent: Nov. 28, 1989

[54] EYELID AND ANTERIOR ORBIT SWAB
[76] Inventor: Sol Hamburg, 9006 Abbeydale, Houston, Tex. 77031
[21] Appl. No.: 93,182
[22] Filed: Sep. 4, 1987
[51] Int. Cl.⁴ .......................... A61F 9/00; A61F 13/00
[52] U.S. Cl. ........................................... 604/1; 604/294
[58] Field of Search ............................ 604/1, 2, 3, 294
[56] References Cited
U.S. PATENT DOCUMENTS

| | | | |
|---|---|---|---|
| 982,232 | 1/1911 | Bartholomew | 604/1 |
| 2,006,539 | 7/1935 | Deford | 604/1 |
| 2,491,274 | 12/1949 | McNeill | 604/1 |
| 2,987,063 | 6/1961 | Glickston . | |
| 3,508,547 | 4/1970 | Deuschle . | |
| 4,036,230 | 7/1977 | Adams | 604/294 |

Primary Examiner—Albert W. Davis, Jr.
Attorney, Agent, or Firm—Bernard A. Reiter

[57] ABSTRACT

An improved swab for use only on the eyelid, whose lateral configuration exceeds its vertical and in which lateral configuration there exists a lateral valley defined by a pair of substantially parallel peaks and in which the proximal peak is lower than the distal peak so as to facilitate engagement and cleansing of the eyelid margin both on the anterior and posterior surfaces thereof simultaneously, and which further includes an antibiotic or other medicant previously infused into the swab to form a prepared immediately usable medicinal instrumentality.

9 Claims, 2 Drawing Sheets

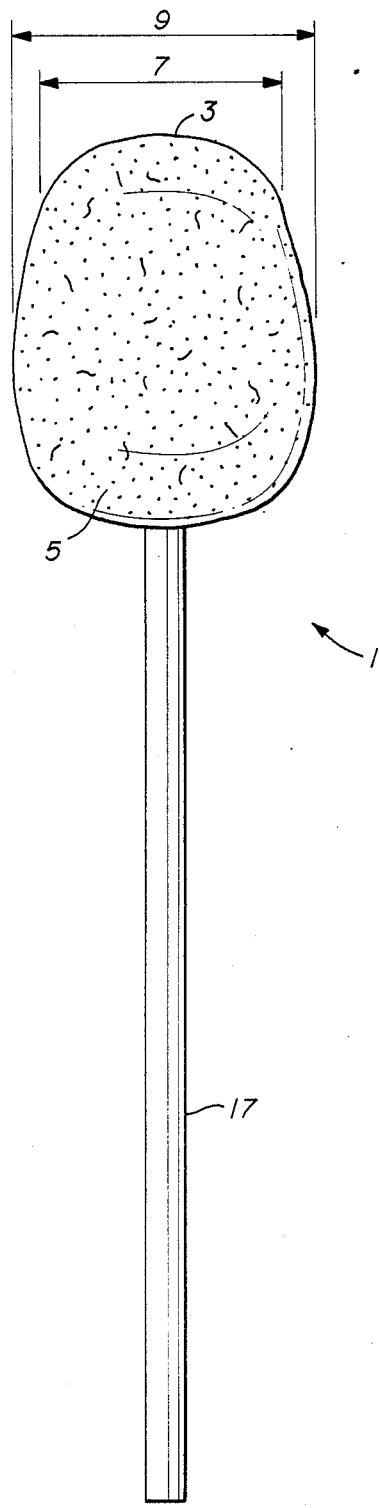
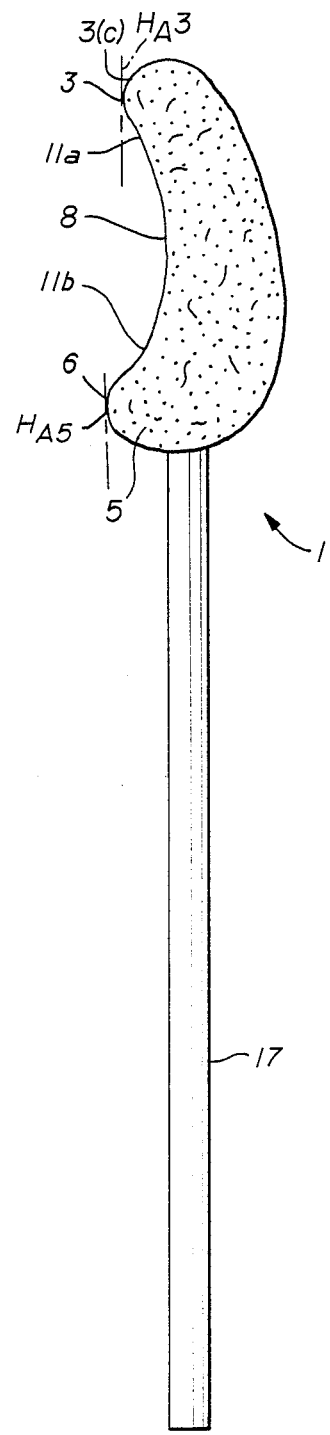
FIG. 1
FIG. 2

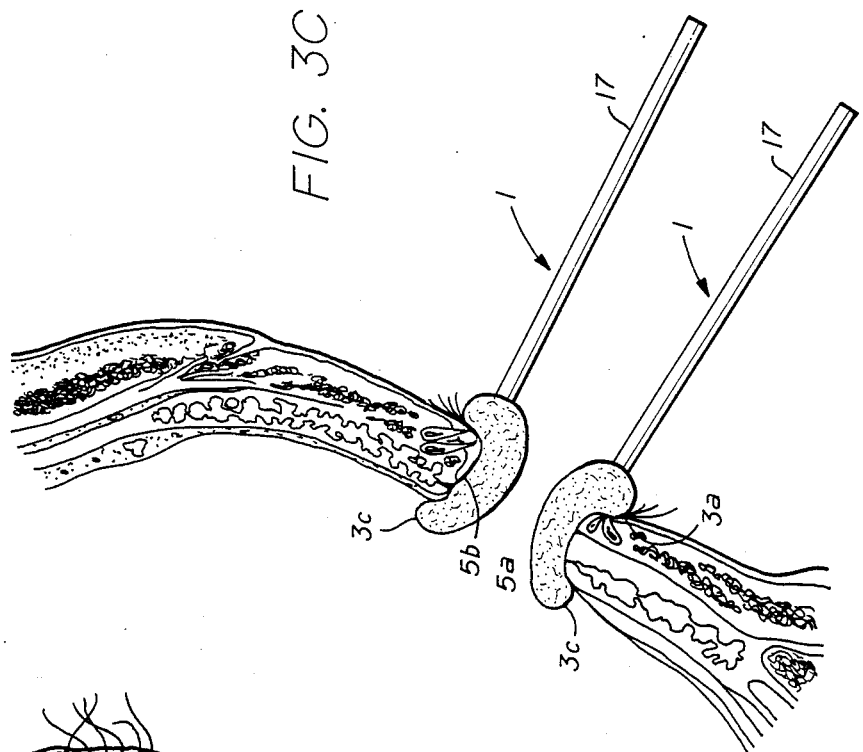
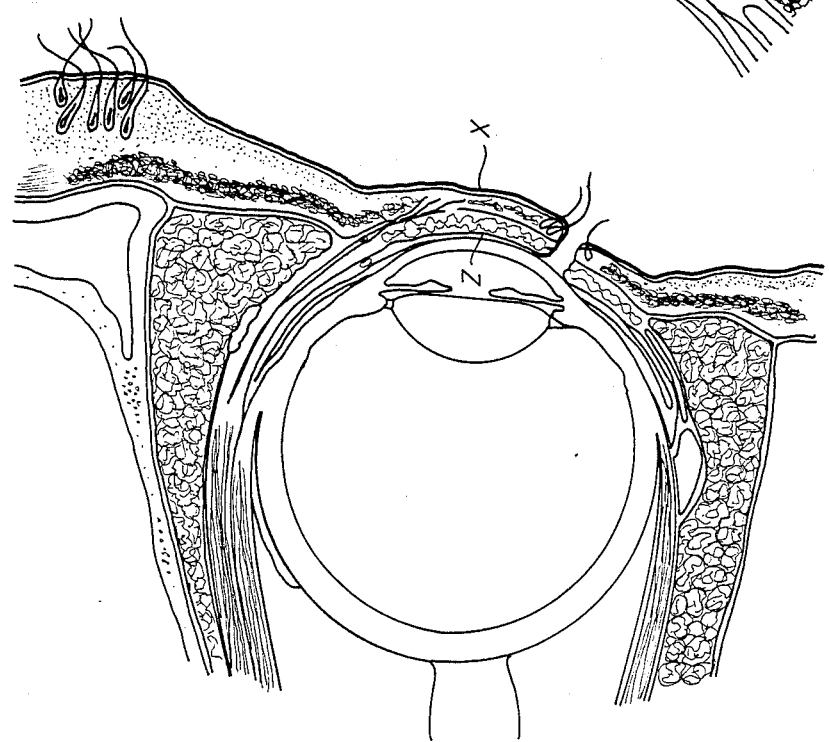
FIG. 3A
FIG. 3B
FIG. 3C

EYELID AND ANTERIOR ORBIT SWAB

The present invention relates to a new and improved medicinal instrument generically referred to as a swab-type applicator made of polyurethane or similar flexible material capable of absorbing and holding a medicant. More particularly, the invention is directed to a pre-prepared medicinal swab specifically devised for ophthalmic use by application of the operative surface of the swab simultaneously to the anterior and posterior lid margin surface, including the meibomian orifices.

BACKGROUND OF THE INVENTION

The preparation of conventional, ready-to-use type swabs or applicators generally involves the use of an absorbent cotton or similar material and in which the material is either wrapped in spiral or transverse fashion around one or both ends of the stick, or is otherwise adhesively attached. All such swabs or applicators are easily unwound and subject to distortion of shape; moreover, the very simplicity and economy of construction of conventional swabs render them inapplicable to more sophisticated uses or uses in sensitive body areas. In addition, such cotton or other material-type swabs are not compressible in use and thus have little of the cushioning effect necessary for delicate applications when pressure may be applied thereto. In view of the fact that such swabs are commonly applied to the skin of human beings, it becomes imperative that the pressure applied to the stick is not transmitted to the skin in an excessive manner, particularly when delicate surfaces of the human anatomy are contacted.

Furthermore, and especially significant in this use, the convexity of conventional swabs precludes adequate application to a complex three-dimensional anatomic structure such as the eyelid margin.

One of the more delicate areas of the human body resides in the area of the eyes. In the eyelids, which are in direct apposition to the globe, are found the meibomian glands, eyelashes and other structures, all of which may be involved in chronic or acute inflammation, either as a result of meibomian gland dysfunction, or secondary to an infection.

While the specific medical treatment of each of these maladies exceeds the explanatory provisions relevant to a description of this invention, it may suffice to state that the entire lid margin of the eye, both anteriorly and posteriorly including the meibomian orifices and eyelashes, must be treated to assure the removal of the sources of the inflammatory process. This may be discharged material at the meibomian orifice, fibrin or cellular debris at the base of the lashes, or bacteria at the lid margin. Further, the cleansing action must be simultaneously delicate so as to avoid aggravation to the preexisting affected area.

Although numerous forms of treatment are devised for inflammation of the eyelid, the more effective of them include the most delicate and uncomplicated procedures. Therefore, hot compresses and lid scrubs with a mild shampoo, along with appropriate local antibiotics applied several times per day, depending upon the severity, are common. The hot compresses are prepared by holding a clean face cloth under the hot water faucet and allowing it to reach a temperature which will effectively heat the eyelids without burning the skin. This dilates the surrounding blood vessels and heats the liquid meibomian secretions, which plug the gland involved. Heating liquifies the stagnate secretions, thereby facilitating drainage through the gland orifice. Frequently, however, cellular and sebaceous debris builds up along either the anterior or posterior lid margin and adjacent lashes. It has been shown that a mechanical action to remove the debris from the affected is an effective treatment for this condition. In such a case it is necessary to initiate direct contact with the lid margin to accomplish cleansing thereof. In that event, the special swab of the invention becomes a necessity, and, due to the construction and configuration thereof, there is provided a marked improvement over presently known swabs in the ability to efficiently cleanse the eyelid margin. The three-dimensional configuration, as well as flexible material used, assures adequate treatment of all affected areas and structures of the lid margin.

In a further feature of the present invention, an appropriate antibiotic ointment or other medicant is used internally of the swab. The medicant is injected into the swab itself prior to use, and typically, in a prepackaged embodiment the medicant may be applied upon direct contact of the swab to the anterior and exterior surfaces of the eyelid margin. This occurs upon application of pressure to the swab to thereby expel the medicant to the swab surface. In this manner there is avoided any smearing of the medicant itself while simultaneously providing an equal distribution of the medicant over the affected areas by merely lightly contacting them with the operative surface of the swab.

These and numerous other features and advantages of the present invention will become obvious upon a careful reading of the following detailed description, claims, and drawings, wherein like numerals denote like parts in the several views and wherein:

DETAILED DESCRIPTION OF THE DRAWINGS

FIG. 1 is a frontal view of the swab of the invention.

FIG. 2 is a side view of the swab of the invention.

FIG. 3(a) is a sectional view through the surrounding structure of an eye.

FIG. 3(b) is a cross-sectional view through an enlarged section of the lower eyelid of FIG. 3(a) and shows the improved swab of the invention in contacted relationship therewith.

FIG. 3(c) is a cross-sectional view through an enlarged section of the upper eyelid of FIG. 3(a) and shows the improved swab of the invention in contacted relationship therewith.

DETAILED DESCRIPTION OF THE INVENTION

The improved swab as shown in FIG. 1 is constructed from a lightweight, porous, soft, sponge-like material which may include genuine sponge, a soft lightweight plastic, or other material which is absorbent in nature and capable of retaining a liquid or ointment content therein and of retaining its configuration while so doing. The material of the swab should have its own memory of configuration. It is essential to the invention that the character of the material of the swab be capable of retaining its specific shape when moist and even when saturated with an antibiotic, steroid, or other medicant, as described hereinafter.

With reference to FIG. 3(b), the configuration of the swab 1 consists of an upper blotting means 3 and a lower blotting means 5, which are respectively adapted to contact the lower frontal surface 3a and the bottom surface 3a of the eyelid margin. The upper blotting means 3 is characterized by a peak 3c in position remote from handle 17. The peak 3c is intended for contact with the upper or lower interior surface of the eyelid margin and is comparatively wide throughout its lateral dimension 7 so that such interior surface of the eyelid can be gently contacted therewith in minimum sequential dabs across the lateral dimension of the muscle so as to remove the lipid meibomian secretions or other cellular debris. Such maximal width on the interior blotting surface is of utmost importance to the effective and beneficial use of the swab. Simultaneously, the lower blotting means 5 of the swab is in contact with the anterior surface 5a of the eyelid, but it is noted that the lateral dimension 9 of the lower blotting means 5 is somewhat larger than the lateral dimension 7 of the upper blotting means 3. The lower blotting means 5 which is characterized by a peak 6 (FIG. 2) proximate to handle 17 is proximate also to the exterior surface of the eyelid. See FIG. 3(a), (b) and (c). An increased contact with the eyelid is thereby accomplished through use of the swab having a slightly increased lateral dimension 9 at the lower blotting means 5 area. There is disposed between the upper blotting means 3 and lower blotting means 5 a valley or concave blotting means 8. It is imperative that this intermediate area of the swab be configured in a gentle concavity such that the defining walls allow for ample space between the upper means 3 and the lower means 5. It is recommended that the opening defined by the walls 11a and 11b of the concave blotting means 8 are substantially greater than an included angle of 90 degrees, but less than 165 degrees, see FIG. 2.

As shown in the drawings, particularly FIG. 2, the horizontal axis HA5 of the lower blotting means 5 is substantially coincident with the horizontal axis HA3 of the upper blotting means 3. However, the operative surface of the concave blotting means 8, through being defined by the aforementioned included angle, is inclined upwardly such that the wall 11b is substantially steeper than the wall 11a. In this manner there is provided a "cupping effect" that enables the concave blotting means to encompass the lower surface 5a of the lid margin while the user of the swab holds it in its first operative position, that is, with the handle or stick 17 pointed down, see FIG. 3(b).

The configuration of the swab facilitates the dabbing application of the swab on the eyelid margin as it is sequentially moved laterally across the exterior and lower surfaces thereof. Upon completion of the dabbing treatment the swab position is reversed, that is, the handle 17 is positioned upwardly (FIG. 3(c)) such that the upper blotting means 3 is moved to a position covering the interior surface of the orbicularis muscle. In this position the lower blotting means 5 is placed in operative position with the anterior surface X of the eyelid. The operative concave blotting means 11 is placed in operative contact with the lower surface because the greater included angle of the concavity enables a comfortable positioning of the upper portion (within the blotting means 3), while the lower blotting means 5 embraces the exterior area. Without such expanded included angle an extreme discomfort may result to the patient particularly in view of the fact that the handle 17 would be co-linearly disposed along the axes of the upper and lower blotting means of the swab 1.

In an alternate form of the invention it is intended that a medicant be carried within the improved swab. This may be done at the point of manufacture or thereafter. In either case the medicant 23 (as shown in ghost in FIG. 1) is introduced such as by injection to the interior of the swab where it inherently remains in the absence of pressure, this being primarily due to the non-absorbent memory-like characteristic of the material here recommended. A packaging, even including a sealed plastic enclosure for the swab may be used to retain the moisture content of the medicant within the swab.

The improved swab of the invention is capable of numerous modifications and improvements without departing from the spirit of the invention here described and yet remain within the scope of the appended claims. For example, the handle 17 may be disposed at an angle to the axis of the upper and lower blotting means so as to facilitate comfortable positioning of the swab portion itself on any of the critical surfaces of the eyelid, namely on the exterior surface X, the anterior surface Z, or the end surfaces 5a and 5b thereof, hereinabove also referred to as a bottom surface. Such positioning of the handle enables a wide variance in the relative contacting position of the concave blotting means 11. It remains essential, however, that the included angle be substantial, as described, and that all surfaces meet one another in gentle curvatures, as is shown in the drawing, where the concave blotting means intersects the upper and lower blotting means surfaces.

Similarly, the intersection of the walls of the concave blotting means 11 at the valley thereof must necessarily result in a gentle curvature, rather than a point intersection. Nevertheless, angular positioning of the included angle with respect to the horizontal axis as shown in FIG. 2 may be varied to accommodate the comfort of individual usage.

What is claimed:

1. An improved swab-type applicator for treatment of the eyelid margin inflammation due to meibomian gland dysfunction or other related infection comprising:
    an upper blotting means
    a lower blotting means,
    each said blotting means being constructed of a lightweight, porous, sponge-like material capable of retaining its configuration when wet,
    each said upper and lower blotting means characterized by an intermediary blotting means,
    said intermediary blotting means consisting of a concave portion of compatible configuration to accommodate any two of the three surfaces of the lid margin so as to enable efficacious treatment by removal of the sebaceous debris or the like simultaneously from either the exterior surface and lower surface or the lower surface and anterior surface of said eyelid margin.

2. The improved swab of claim 1 wherein the included angle of said concave intermediary blotting means is substantially greater than 90 degrees or more but less than 165 degrees and wherein the valley thereof is of curvature greater than the angle of intersection between the lower surface and either the exterior or anterior surfaces of the eyelid margin.

3. The improved swab of claim 1 wherein the concave blotting means residing intermediate the upper and lower blotting means rests principally adjacent to the lower blotting means.

4. The improved swab of claim 1 where there is included a handle affixed to the swab for manually moving the swab during treatment of the eyelid margin, from a position either beneath the eyelid margin and with which the swab is moved to a position above the eyelid margin.

5. The improved swab of claim 2 wherein each said upper and lower blotting means is characterized respectively by a lateral dimension in which said dimension of the upper blotting means is less than the lateral dimension of the lower blotting means so as to facilitate principal dabbing treatment by the upper blotting means while the lower blotting means simultaneously absorbs secretions from the eyelid margin, thereby reducing the potential tearing by the user.

6. The improved swab of claim 5 wherein the upper blotting means is in a position remote from said handle and the lower blotting means is in a position proximate to said handle and wherein the lower blotting means is thicker in cross-section than the upper blotting means so as to facilitate treatment of the eyelid margin with the upper blotting means while said lower blotting means is in greater pressure contact with the lower blotting means.

7. An improved swab for use on the eyelid margin for treatment of disease and/or irritation thereto by facilitating removal of cellular and sebaceous debris buildup along either the anterior or exterior lid margin and adjacent lashes with a mechanical action while minimizing contact to and irritation of the treated area comprising:

a blotting means surface of concave configuration and in which the walls of the concave configuration consist of an upper wall and a lower wall, and an included angle therebetween of configuration to enable contact with either or both the exterior and anterior lower surface of the upper eyelid margin, and the lower exterior and anterior of the eyelid margin while facilitating a swabbing moving action thereacross, the upper surface of said concave blotting means terminating in an upper blotting means and the lower surface of said blotting means terminating in the lower blotting means, each said upper and lower blotting means being characterized respectively by a lateral dimension in which said dimension of the upper blotting means is less than the lateral dimension of the lower blotting means so as to facilitate principle dabbing treatment by the upper blotting means while the lower blotting means simultaneously absorbs secretions from the eyelid margin, thereby reducing the potential tearing by the user.

8. The improved swab of claim 7 in which a medicant is contained internally of the swab so that the application of pressure to the swab expels the medicant to the swab surface.

9. The swab of claim 8 wherein the swab is encased within a sealed enclosure for storage and/or shipment to ensure cleanliness and inhibit evaporation of the medicant.

* * * * *